United States Patent [19]
Clifton

[11] Patent Number: 5,486,204
[45] Date of Patent: Jan. 23, 1996

[54] METHOD OF TREATING A NON-PENETRATING HEAD WOUND WITH HYPOTHERMIA

[75] Inventor: Guy L. Clifton, Houston, Tex.

[73] Assignee: University of Texas Health Science Center Houston, Houston, Tex.

[21] Appl. No.: 309,202

[22] Filed: Sep. 20, 1994

[51] Int. Cl.$^6$ .................................................. A61F 7/00
[52] U.S. Cl. ........................... 607/96; 128/736; 128/748
[58] Field of Search ........................... 607/96, 108–112, 607/104; 128/748, 898, 736

[56] References Cited

U.S. PATENT DOCUMENTS

| | | |
|---|---|---|
| 4,750,493 | 6/1988 | Brader . |
| 4,920,963 | 5/1990 | Brader . |
| 4,987,896 | 1/1991 | Nakamatsu ........................... 607/109 |
| 5,236,908 | 8/1993 | Gruber et al. . |
| 5,261,399 | 11/1993 | Klatz et al. . |

*Primary Examiner*—Angela D. Sykes
*Attorney, Agent, or Firm*—Gunn & Associates

[57] ABSTRACT

A method of treating severe brain trauma with hypothermia includes the introduction of specified medication to reduce the risk of cardiac arrhythmia and other malfunctions that may result from the brain trauma or the hypothermia. The method further includes a protocol for the treatment which defines time, temperature, rate of change of temperature, and the timing of the introduction of medications. Finally, rigidly controlled rewarming reduces the incidence of rewarming shock in recovering patients.

6 Claims, No Drawings

METHOD OF TREATING A NON-PENETRATING HEAD WOUND WITH HYPOTHERMIA

FIELD OF THE INVENTION

The present invention relates generally to the field of the treatment of severe, non-penetrating head wounds and, more particularly, to a method of assisting in the recovery from head trauma through the use of hypothermia.

BACKGROUND OF THE INVENTION

The mortality rate from severe traumatic brain injury (TBI) in the United States alone amounts to 9–30 deaths per 100,000. Those suffering brain injury requiring medical treatment number 160–300 per 100,000, with approximately 20 percent of patients admitted to treatment facilities sustain a moderate to severe degree of injury as measured by the Glasgow Coma Score (GCS) of 3–12. Direct costs of brain injury, including the costs of treatment and long-term care, as well as indirect costs including disablement and the loss of productivity of brain injury patients and other such costs, are staggering.

Profound hypothermia has long been recognized as an effective means of cerebral protection from global ischemia. Clinical application of surface cooling to profound levels without extracorporeal bypass has been limited, however, because of the occurrence of ventricular fibrillation at temperatures below 27° C. From 1974–1980, researchers reported successful total circulatory arrest using extracorporeal bypass at 10° to 20° C. for up to 50 minutes for repair of cardiac anomalies in children less than one year of age. Later, total circulatory arrest at temperatures of 8°–10° C. was also used in repair of adults' ascending aortic arch aneurysms.

These techniques of protection from global ischemia are in use today. However, the problem of intracranial hemorrhage during rewarming, together with the necessity of large vessel cannulation, has limited the application of hypothermia to surgical techniques.

Moderate hypothermia, in the range of 30°–33° C., is known to diminish brain tissue loss in laboratory animals when hypothermia is administered during and after ischemia. Improved behavioral outcome and reduced mortality have also been observed in such animals with moderate systemic hypothermia administered after injury. Moderate hypothermia has also been found to diminish excessive toxic neurotransmitter release and to prevent disruption of the blood-brain barrier in the test subjects of fluid percussion brain injury.

The potential clinical utility of moderate systemic hypothermia in treatment of patients with severe brain injury was investigated as early as 1958. There are reports of over 120 patients with severe brain injury producing coma who were treated with systemic cooling. All that can be concluded from this clinical literature is that toxicity is probably low at temperatures 30° C. or greater and durations of less than 72 hours. The likely sources of toxicity from systemic cooling are coagulopathy, pulmonary complications, and cardiac ventricular arrhythmias.

Induced localized hypothermia has been used widely in the non- or pre-hospital treatment of numerous physiologic conditions. Cold packs of some sort are standard equipment in first aid kits, and are used to decrease peripheral blood flow (and commensurate swelling) in the event of contusion, insect bites or stings, nosebleeds, sprains, etc. Cold compresses to the head, of course, have long been a standard symptom-relieving measure for headaches and fever.

Brader, U.S. Pat. No. 4,750,493 disclosed a method of preventing brain damage during cardiac arrest, CPR, or severe shock. The method taught by Brader included cooling the extracranial area including the face during emergency care of cardiac arrest or severe shock. This spatially limited cooling method was suggested to promote maximum perfusion to the brain while lowering the oxygen demand of brain cells. However, this method did not encompass cooling of the entire body but of the head alone. Limitations of this technique are related to attempting to cool the head locally while warm blood circulates through the brain. In other words, Brader does not suggest or even relate to total systemic hypothermia. Further, Brader failed to appreciate the special difficulties involved in the treatment of severe brain trauma and required a hood- or cap-like topical cold pack to implement his method. Also nothing in Brader identifies the protocol for the introduction of medication to control toxicity or the rate at which a patient is to be returned to normal body temperature following the treatment, referred to herein as "rewarming".

Aside from topical and spatially limited cold applications, conventional hypothermia (body temperature less than 30° C.) has been known to reduce brain metabolic requirements, which may lessen cerebral edema and neuropathological damage. Therefore, conventional hypothermia has been used in combination with barbiturate therapy to treat brain swelling and intracranial hypertension.

However, the aggressive use of conventional hypothermia has been abandoned during the past decade because (1) it was difficult to keep the body's core temperature at 30° C. for several days; (2) clinical outcome was never shown to be improved by the technique; (3) cardiovascular instability often occurred during conventional hypothermia; and (4) the specific parameters of the depth of hypothermia, the duration of the hypothermia, and the method of rewarming were never established. Nor was the depth or duration of hypothermia specified by Brader.

Several recent experimental studies have suggested a protective effect of mild hypothermia on the brain during anoxia, hypoxia, and following head injury. It is known that a decrease in body temperature of 1° C. to 3° C. can minimize or prevent brain energy failure during hypoxia. Similar observations have led some clinicians to employ mild hypothermia in the treatment of brain swelling and intracranial hypertension. However, these observations have failed to identify a specific protocol to significantly improve the long term prognosis of head injury patients. Further, the use of hypothermia alone, without the identification of such a specific protocol, particularly in combination with the application of medications, has yet to address the problem of toxicity from systemic cooling in the patient.

The prior art has also failed to adequately address problems associated with so-called "rewarming shock." Rewarming shock has been shown to create troublesome complications of hypovolemic shock and abrupt intra-cranial pressure elevation when a patient's core temperature is returned to normal body temperature from an extended period of hypothermia. It is generally believed that vasodilation can often lead to a low arterial pressure during this rewarming phase.

Thus, there remains a need for a controllable and easily administered method of treating the victims' of severe brain trauma to achieve the perceived benefits of hypothermia.

Such a method should preferably include the administration of medications to control both the effects of the brain injury and to balance the potential deleterious effects to the body of being subjected to reduced temperatures for an extended period. Effective hypothermia treatment should also control the desired depth of hypothermia, the optimal duration of hypothermia, and the rate and period of rewarming the patient and clearly identify when the administration of medications should be terminated.

SUMMARY OF THE INVENTION

The present invention solves these problems of the prior art with an experimentally verified protocol for the treatment of severe brain trauma using hypothermia.

This protocol begins with the identification of which patients are likely to benefit from the administration of the present invention. It has been found that the method of the present invention should begin as soon as possible, and certainly within six hours of the severe brain injury. If the patient is a satisfactory candidate, the cooling process commences.

Simultaneously, or during the cooling process, a muscle relaxant and a sedative are administered in the manner commonly used in the art for the conventional treatment of brain trauma. The cooling process continues until the intravascular temperature of the patient is reduced to at least about 33° C. but no lower than about 32° C. The administration of a muscle relaxant and sedative are continued while the patient is maintained at 32°–33° C. for at least about 48 hours. Then, the patient is gradually restored to normal body temperature at a slow, controlled rate, preferably about 1° C. every four hours. Once the patient's temperature reaches about 35° C., medication is discontinued.

These and other features and advantages of the present invention will be immediately apparent to those of skill in the art as they review the following detailed description.

DETAILED DESCRIPTION OF A PREFERRED EMBODIMENT

Background

The present invention comprises a method treating severe brain injury with a carefully controlled combination of hypothermia and medication at specified times, durations, and rates of change. While each of the individual components of the present invention have shown promise in the treatment of brain trauma, the present invention now provides a comprehensive protocol with verified results.

The specific parameters in the following detailed description are the presently preferred embodiment of the present invention and have shown the greatest likelihood of success in carrying out this invention. However, modifications by those of skill in the art to the technique described, including variations of these parameters, are fully within the scope and spirit of the present invention.

Test Results

The criteria for including subjects in tests that provided the following results were patients ages 16 to 60 years with post-resuscitation GCS of 4 to 7 after nonpenetrating brain injury. Subjects were excluded from these results if they suffered from hypoxia after resuscitation ($O_2$ saturation <94% for >30 min.), major systemic injuries requiring laparotomy, pulmonary failure, or sustained hypotension after resuscitation (systolic blood pressure ≤90 mmHg for ≥2 hours). Patients were also excluded if cooling could not be initiated with 6 hours of injury.

Randomization was stratified into two groups, GCS 4 and 5 and GCS 6 and 7, to obtain balance in injury severity in the two groups. Initial patient management consisted of rapid intubation and ventilatory support (usually done prior to admission), early computerized tomographic (CT) scanning, and surgical procedures for hematomas. Either fiberoptic or ventricular catheters were placed for intracranial pressure (ICP) monitoring. Ninety-five percent of the patients were transported by helicopter from the road side or from another hospital's emergency department within 2 hours of injury. CT scans were performed in the emergency department and craniotomies for hematomas were performed immediately. Placement of arterial catheters, internal jugular catheters, and Foley catheters was routine.

Patients undergoing hypothermia or requiring treatment with mannitol also had placement of SwanoGanz catheters. In the absence of increased ICP, $PaCO_2$ was maintained at 30 to 35 mmHg. Increased ICP was managed first by hyperventilation to $PaCO_2$ 25 to 30 mmHg using jugular venous saturation of 50% to determine the lowest level of hyperventilation. Morphine-sulfate (10–20 mg) and metocurine (10–20 mg IV) were used hourly to control ventilation. Mannitol was given for ICP greater than 200 mmHg after hyperventilation until a serum osmolality of 315 mosm or greater was reached. In the preferred embodiment, the muscle relaxant comprises vecuronium.

Fluids were replaced so that pulmonary capillary wedge pressure was 8 mmHg or more. All patients were given phenytoin 18 mg/kg body weight and maintained at therapeutic phenytoin blood levels thereafter. Feeding was begun within 72 hours of injury by nasojejunal tube placed endoscopically or by parenteral nutrition. Serum glucose was maintained at less than 200 mg/dl in all patients.

In the control group, patients were treated with standard management at normothermia and were kept at 37° C. by use of cooling blankets and acetaminophen for 80 hours after injury. In the hypothermia group, cooling was induced by securely wrapping the patients in cooling blankets set at 5° C. Metocurine 10 mg/hour and morphine-sulfate 10 mg/h were given continuously. These medications were discontinued when the patient was warmed to a temperature of 35° C. unless ICP was greater than 200 mmHg. Intravascular temperatures from the Swan-Ganz catheter were used for temperature measurement in the hypothermia group. Bladder or rectal temperatures were used in the normothermia group.

Warming was begun 48 hours after a temperature of 33° C. was first reached and patients were warmed at 1° C. every 4 hours. Serum potassium was measured every 6 hours during the first 72 hours and maintained at 3.5 to 5.0 mEq/L by intravenous potassium administration. Blood gasses were not corrected for temperature but were measured and interpreted at 37° C. Complete blood count, prothrombin time (PT), and partial thromboplastin time (PTT) were measured daily for 4 days for all patients and were measured at 37° C. Records of all complications during hospitalization were kept. Therapy intensity level is a numerical score quantifying $PaCO_2$, mannitol dosage, muscle relaxant use, and sedation as treatments for elevated ICP. This was computed hourly for all patients during ICP monitoring. The Glasgow Outcome Scale (GOS) was assessed at 3 months after injury.

GOS score distribution between groups was compared by chi-square test. Physiologic and laboratory data were analyzed in four blocks of time: the first 12 hours (cooling), the next 48 hours (steady state at 32°–33° C.), the next 12 hours (rewarming), and the subsequent 12 hours (steady state after rewarming) for a total of 84 hours after injury. Bonferroni's test was used to compare the mean values for each patient in each time block for both laboratory and physiologic data. Repeated measures analysis of variance showed interaction effects between treatment and time period for all variables except ICP for which 0.05 was greater than the p value, which was less than 10.

Results

The characteristics of the two groups that most affect outcome are shown in Table 1. Age and GCS distribution were not significantly different in the two groups. Distribution by pupillary reactivity and primary diagnosis was similar. The mean temperature on admission for all patients was 36.2°±1.3° C. (SE) at 2.7±1.6 hours after admission. To bring patients to 33° C. required 7.88±0.61 (SE) hours from admission. Rewarming was started 48 hours after the patient's temperature reached 33° C., as 12 to 14 hours were used to bring patients from 33° to 37° C.

Heart rate was significantly lower in the hypothermia group only in the second time period when hypothermia resulted in bradycardia (Table 2). Mean arterial pressure (MAP) was significantly different in the two groups only in the third time period with a 13 mmHg lower MAP in the hypothermia group. Cerebral perfusion pressure (CPP) was 16 mmHg lower in the hypothermia group in the third time period with a mean value in normothermia of 80.9±3.42 mmHg and in the hypothermia group of 64.96±2.13 mmHg. Morphine and metocurine doses were higher in the hypothermia group in the first three time periods (Table 3). Mean $PaCO_2$ was 31.0±0.89 mmHg in the normothermia group and 30.8± 0.83 mmHg in the hypothermia group in the second time period.

Hypothermia is known to induce an intracellular shift of potassium and cooling of blood prolongs PT and PTT. Table 4 details the means and standard error of PT, PTT, serum potassium, and serum glucose in the two groups of patients. PT was measured daily for 4 days and was slightly but significantly prolonged in the third and fourth time periods. PTT was normal and not different in the two groups in the first time block and the second time period. PTT in the normothermia group in the third time period was 32.62±1.14 sec and slightly prolonged at 34.62±1.01 sec in the hypothermia group (p<0.025). PTT was also slightly prolonged in the fourth time period in hypothermia patients with a PTT in normothermia patients of 31.66±0.61 sec and in the hypothermia group of 37.05±3.11 sec (p<0.001). Serum potassium was within a normal range in both groups in the first three time periods. Serum potassium was slightly increased after rewarming in the fourth time period in the hypothermia group. This was due to potassium replacement in the hypothermia group during cooling with potassium mobilization during rewarming. The hypothermia group received 65% more potassium administered than the normothermia group during the 84 hours of measurement. Serum glucose was increased in the hypothermia group in the second time period.

Complications are shown in Table 5. The incidence of sepsis was higher in the hypothermia group, though the difference was not statistically different. The incidence of seizures was lower in the hypothermia group. The mortality rate was 8 of 22 patients (36%) in the normothermia group and 8 of 23 patients (35%) in the hypothermia group. There were no cardiac complications or coagulopathy-related complications in either group.

There was a strong indication of improved neurologic outcome in the hypothermia group. GOS scores were combined into two categories: GR/MD and SD/V/D. In the normothermia group, 36.4% of patients were in the GR/MD group and 63.6% were in the SD/V/D group. In the hypothermia group, 52.2% were in the GR/MD group and 47.8% were in the SD/V/D group. These differences were not significant by chi-square analysis (p=0.287) but show a positive trend. GOS distributions are illustrated in Table 6. These distributions are divided into two groups: Good Recovery/Moderate disability (GR/MD) and Severe Disability/Vegetative/Dead (SD/V/D).

Hypothermia drives potassium intracellularly producing hypokalemia. The present invention preferably includes potassium replacement until serum potassium is normalized. The possibility of rebound hyperkalemia during rewarming may be of concern but the specified rate of rewarming maintains serum potassium in the normal range. Acid-base management is guided by blood-gas analysis not corrected for temperature but measured at 37° C. (alpha stat). In order to maintain $PaCO_2$ of 30 to 35 mmHg, ventilatory rates must be decreased during hypothermia because of systemic hypometabolism.

In the present disclosed method, 48 hours has been selected as the longest time period for maintaining steady-state hypothermia. In animals, toxicity from moderate hypothermia occurs both as the temperature is decreased and as the duration of hypothermia is increased. Coagulopathy and necrosis occur after 3 days of moderate hypothermia in dogs. Mortalities occur after 48 hours of hypothermia in monkeys and dogs. The duration of 48 hours has proved to produce minimal complications with evidence of benefit in functional outcome.

The principles, preferred embodiment, and mode of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

TABLE 1

| | | PATIENT CHARACTERISTICS | |
|---|---|---|---|
| | | Normothermia (n = 22) | Hypothermia (n = 24) |
| Age (yrs) | 15–25 | 11 | 12 |
| | 26–35 | 4 | 7 |
| | 36–45 | 3 | 4 |
| | 46–55 | 3 | 1 |
| | >55 | 1 | 0 |
| Glasgow Coma | Scale | | |

TABLE 1-continued

PATIENT CHARACTERISTICS

|  |  | Normothermia (n = 22) | Hypothermia (n = 24) |
|---|---|---|---|
| Score | 4–5 | 9 | 12 |
|  | 6–7 | 13 | 12 |
| Primary diagnosis | Epidural hemotoma | 1 | 0 |
|  | Subdural hemotoma | 5 | 8 |
|  | Intracerebral hemotoma | 1 | 0 |
|  | Diffuse Brain Injury | 15 | 16 |
| Pupillary reactivity | Reactive | 17 | 16 |
|  | Unilaterally nonreactive | 2 | (4 orbital injuries) |
|  | Bilaterally nonreactive | 3 | 4 |

TABLE 2

RESULTS: TEMPERATURE, HEART RATE, MAP, ICP, AND CPP

| Hrs after ER admission | Normothermia mean | SE | Hypothermia mean | SE | Bonferroni p value |
|---|---|---|---|---|---|
| Temp (°C.) |  |  |  |  |  |
| 0–11 | 36.98 | 0.021 | 34.69 | 0.26 | p < 0.001 |
| 12–59 | 37.51 | 0.12 | 33.05 | 0.14 | p < 0.001 |
| 60–71 | 37.70 | 0.16 | 35.35. | 0.25 | p < 0.001 |
| 72–83 | 37.52 | 0.16 | 37.05 | 0.19 | NS |
| Heart rate (bpm) |  |  |  |  |  |
| 0–11 | 95.71 | 3.67 | 88.47 | 3.18 | NS |
| 12–59 | 97.21 | 3.35 | 71.49 | 3.16 | p < 0.001 |
| 60–72 | 97.45 | 4.25 | 97.92 | 3.80 | NS |
| 73–83 | 101.45 | 4.84 | 110,61 | 3.88 | NS |
| MAP (mmHg) |  |  |  |  |  |
| 0–11 | 96.95 | 3.16 | 97.00 | 2.10 | NS |
| 12–59 | 92.00 | 3.07 | 87.10 | 2.20 | NS |
| 60–72 | 96.01 | 2.50 | 83.37 | 1.83 | p < 0.001 |
| 73–83 | 96.06 | 3.04 | 87.99 | 2.28 | NS |
| ICP (mmHg) |  |  |  |  |  |
| 0–11 | 11.02 | 1.91 | 10.80 | 0.97 | NS |
| 12–59 | 18.32 | 3.61 | 12.96 | 0.99 | NS |
| 60–72 | 17.04 | 2.06 | 18.09 | 1.49 | NS |
| 73–83 | 19.19 | 2.34 | 16.11 | 0.82 | NS |
| CPP (mmHg) |  |  |  |  |  |
| 0–11 | 87.13 | 3.61 | 87.32 | 2.34 | NS |
| 12–59 | 80.44 | 2.21 | 74.23 | 2.13 | NS |
| 60–72 | 80.90 | 3.42 | 64.96 | 2.13 | p < 0.001 |
| 73–83 | 77.07 | 4.56 | 73.52 | 2.27 | NS |

TABLE 3

RESULTS: MORPHINE AND METOCURINE

| Hrs after ER admission | Normothermia mean | SE | Hypothermia mean | SE | Bonferroni p value |
|---|---|---|---|---|---|
| Morphine (mg/h) |  |  |  |  |  |
| 0–11 | 1.72 | 0.39 | 4.75 | 0.63 | p < 0.001 |
| 12–59 | 3.35 | 0.66 | 9,93 | 0.82 | p < 0.001 |
| 60–72 | 3.71 | 1.02 | 7.85 | 0.78 | p < 0.01 |
| 73–83 | 3.98 | 0.97 | 5.52 | 0.97 | NS |
| Metocurine (mg/h) |  |  |  |  |  |
| 0–11 | 0.87 | 0.33 | 4.56 | 0.61 | p < 0.001 |
| 12–59 | 2.26 | 0.63 | 9.38 | 0.79 | p < 0.001 |
| 60–72 | 3.00 | 1.08 | 7.10 | 0.60 | p < 0.005 |
| 73–83 | 2.52 | 0.68 | 5.27 | 0.98 | p < 0.10 |

TABLE 4

RESULTS: MEAN AND SE OF PT, PTT, POTASSIUM, AND GLUCOSE

| Hrs after ER admission | Normothermia mean | SE | Hypothermia mean | SE | Bonferroni p value |
|---|---|---|---|---|---|
| PT |  |  |  |  |  |
| 0–11 | 13.80 | 0.23 | 13.31 | 0.19 | NS |
| 12–59 | 13.02 | 0.17 | 13.04 | 0.12 | NS |
| 60–72 | 12.47 | 0.29 | 12.86 | 0.21 | p < 0.05 |
| 73–83 | 12.13 | 0.30 | 12.93 | 0.23 | p < 0.001 |
| PTT |  |  |  |  |  |
| 0–11 | 30.93 | 1.03 | 28.65 | 0.92 | NS |
| 12–59 | 30.88 | 0.57 | 33.13 | 1.13 | NS |
| 60–72 | 32.62 | 1.14 | 34.62 | 1.01 | p < 0.025 |
| 73–83 | 31.66 | 0.61 | 37.05 | 3.11 | p < 0.001 |
| Potassium |  |  |  |  |  |
| 0–11 | 3.79 | 0.07 | 3.65 | 0.10 | NS |
| 12–59 | 3.80 | 0.05 | 3.75 | 0.05 | NS |
| 60–72 | 3.76 | 0.08 | 4.03 | 0.13 | NS |
| 73–83 | 3.80 | 0.09 | 4.24 | 0.14 | p < 0.005 |
| Glucose |  |  |  |  |  |
| 0–11 | 186.82 | 12.31 | 177.52 | 13.34 | NS |
| 12–59 | 158.31 | 5.79 | 195.38 | 9.30 | p < 0.01 |
| 60–72 | 154.72 | 8.03 | 194.05 | 20.62 | NS |
| 73–83 | 174.74 | 12.17 | 206.91 | 20.23 | NS |

TABLE 5

COMPLICATIONS

|  | Normothermia | Hypothermia |
|---|---|---|
| Acute respiratory distress syndrome | 2 | 2 |

TABLE 5-continued

| COMPLICATIONS | | |
| --- | --- | --- |
| | Normothermia | Hypothermia |
| Pneumonia | 7 | 9 |
| Sepsis | 4 | 9 |
| Seizures | 5 | 0 |
| Pancreatitis | 1 | 0 |
| Cardiac arrhythmias | 1 | 0 |
| Renal failure | 1 | 2 |
| Uncontrollable ICP | 6 | 7 |

TABLE 6

| GOS DISTRIBUTION | | | |
| --- | --- | --- | --- |
| | | GR/MD | S/V/D |
| Normothermia | n | 8 | 14 |
| | % | 36.4 | 63.6 |
| Hypothermia | n | 12 | 11 |
| | % | 52.2 | 47.8 |

I claim:

1. A method of treating brain injury in a human patient comprising the steps of (1) beginning to cool the patient within 6 hours of the brain injury;

(2) beginning the introduction of a muscle relaxant and a sedative during the cooling step (1);

(3) continuing to cool the patient to 33° C. intravascular temperature;

(4) maintaining the patient at 32°–33° C. for 48 hours, continuing the introduction of muscle relaxant and sedative during the maintaining step (4);

(5) warming the patient at a rate of 1° C. per 4 hours;

(6) discontinuing the introduction of muscle relaxant and sedative when intravascular temperature reaches 35° C.; and (7) discontinuing the warming step when the patient reaches normal body temperature.

2. The method of claim 1 wherein the step of cooling includes the steps of applying a cooling blanket to the patient and setting the blanket to 5° C.

3. The method of claim 1 wherein the muscle relaxant comprises vecuronium and the sedative comprises an opiate.

4. The method of claim 1 further comprising the step of monitoring intracranial pressure of the patient.

5. The method of claim 1 wherein the patient temperature is monitored by bladder temperature.

6. The method of claim 1 further comprising the step of introducing replacement potassium into the patient.

* * * * *